(12) United States Patent
Nishimura et al.

(10) Patent No.: US 10,737,108 B2
(45) Date of Patent: Aug. 11, 2020

(54) OPTICAL TREATMENT DEVICE

(71) Applicant: JMEC CO., LTD., Tokyo (JP)

(72) Inventors: Hiroyuki Nishimura, Tokyo (JP); Samuel Bohman, Tokyo (JP)

(73) Assignee: JMEC CO., LTD., Tokyo (JP)

( * ) Notice: Subject to any disclaimer, the term of this patent is extended or adjusted under 35 U.S.C. 154(b) by 229 days.

(21) Appl. No.: 15/829,403

(22) Filed: Dec. 1, 2017

(65) Prior Publication Data
US 2018/0169432 A1    Jun. 21, 2018

(30) Foreign Application Priority Data

Dec. 19, 2016    (JP) .................................. 2016-245486

(51) Int. Cl.
*A61N 5/06* (2006.01)
*A61M 5/32* (2006.01)
(Continued)

(52) U.S. Cl.
CPC ............ *A61N 5/0601* (2013.01); *A61B 18/22* (2013.01); *A61M 5/1582* (2013.01); *A61M 5/329* (2013.01); *A61M 5/3294* (2013.01); *A61B 2018/00047* (2013.01); *A61B 2018/00291* (2013.01); *A61B 2018/00458* (2013.01); *A61B 2018/2005* (2013.01); *A61B 2018/2255* (2013.01); *A61B 2090/036* (2016.02);
(Continued)

(58) Field of Classification Search
CPC ............ A61N 5/0601; A61N 2005/007; A61N 2005/0602; A61N 2005/0612; A61N 2005/063; A61N 2005/067; A61M 5/329; A61M 5/20

USPC ........................................................... 607/88
See application file for complete search history.

(56) References Cited

U.S. PATENT DOCUMENTS

| 4,592,353 A | 6/1986 | Daikuzono |
| 6,168,591 B1* | 1/2001 | Sinofsky .................. A61L 2/10 606/15 |

(Continued)

FOREIGN PATENT DOCUMENTS

| JP | S57-029345 A | 2/1982 |
| JP | S61-502168 A | 10/1986 |

(Continued)

OTHER PUBLICATIONS

Nov. 14, 2017 Office Action issued in Japanese Patent Application No. 2016-245486.

*Primary Examiner* — Erin M Piateski
(74) *Attorney, Agent, or Firm* — Oliff PLC

(57) ABSTRACT

An injection needle has an opening at a distal end thereof the injection needle and defines a hole. An optical fiber is configured to output a light from a light source and inserted in the hole. The optical fiber has a distal end positioned on an inner side of the opening. A protector is configured to transmit the light and is positioned further towards an opening side of the injection needle than the distal end. The protector is configured to prevent adherence of tissue to the optical fiber. The light emitted from the optical fiber is configured to irradiated onto a treatment target in a state in which the injection needle is inserted into skin, the distal end is positioned on an inner side of the opening, and the protector is positioned further towards the opening side of the injection needle than the distal end.

6 Claims, 4 Drawing Sheets

(51) Int. Cl.
  *A61B 18/22* (2006.01)
  *A61M 5/158* (2006.01)
  *A61N 5/067* (2006.01)
  *A61N 5/00* (2006.01)
  *A61M 5/20* (2006.01)
  *A61B 90/00* (2016.01)
  *A61B 18/00* (2006.01)
  *A61B 18/20* (2006.01)

(52) U.S. Cl.
  CPC . *A61B 2090/049* (2016.02); *A61B 2090/0427* (2016.02); *A61M 5/20* (2013.01); *A61M 2005/3201* (2013.01); *A61N 2005/007* (2013.01); *A61N 2005/0602* (2013.01); *A61N 2005/063* (2013.01); *A61N 2005/067* (2013.01); *A61N 2005/0612* (2013.01)

(56) References Cited

U.S. PATENT DOCUMENTS

| | | |
|---|---|---|
| 2002/0120260 A1 | 8/2002 | Morris et al. |
| 2004/0030369 A1 | 2/2004 | Kubota |
| 2015/0273236 A1* | 10/2015 | Rogers ................ A61N 5/0624 607/80 |

FOREIGN PATENT DOCUMENTS

| | | |
|---|---|---|
| JP | H04-128762 U | 11/1992 |
| JP | H08-126712 A1 | 5/1996 |
| JP | 2002-200181 A | 7/2002 |
| JP | 2005-504560 A | 2/2005 |
| JP | 2005-237963 A | 9/2005 |

* cited by examiner

OPTICAL TREATMENT DEVICE

CROSS REFERENCE TO RELATED APPLICATION

This application claims priority from Japanese Patent Application No. 2016-254486 filed Dec. 19, 2016. The entire content of the priority application is incorporated herein by reference.

TECHNICAL FIELD

The present disclosure relates to an optical treatment device for treating an affected area with light such as a laser.

BACKGROUND

Devices for performing treatment by irradiating a treatment target with light such as a laser have previously been proposed. For example, laser treatment devices which serve as devices for treating a treatment target such as a port wine stain, strawberry mark, and telangiectasia so-called vascular lesions are available, and perform treatment by irradiating vascular lesions with a laser (see Japanese Patent Application Publication No. 2005-237963 and Japanese Patent Application Publication No. H08-126712, for example).

SUMMARY

However, in conventional laser treatment devices, a laser is radiated towards vascular lesions from a location on an outer side of the skin, hence a major part of the laser is absorbed by melanosomes present in the epidermis. For this reason, it is difficult for the laser to reach the vascular lesions located in the dermis, making it impossible to cause sufficient damage to the vascular lesions, and allowing for regeneration or reoccurrence of blood vessels. When the laser is adjusted so as to cause sufficient damage to the vascular lesions located in the dermis, the epidermis is damaged, and thermal side effects such as scarring, keloids, erythema, and post-inflammatory hyperpigmentation are caused by the conduction of heat from the epidermis.

Accordingly, an object of the present disclosure is to provide an optical treatment device which is capable of reliably and efficiently radiating light onto a treatment target, and is capable of suppressing reoccurrence.

An optical treatment device in accordance with one or more embodiments includes a light source configured to output light, an injection needle, an optical fiber, and a protector. The injection needle has an opening at a distal end thereof the injection needle and defines a hole therein. The optical fiber is configured to output the light from the light source and inserted in the hole in the injection needle. The optical fiber has a distal end positioned on an inner side of the opening of the injection needle. The protector is configured to transmit the light emitted from the optical fiber and is positioned further towards an opening side of the injection needle than the distal end of the optical fiber. The protector is configured to prevent adherence of tissue to the optical fiber. The light emitted from the optical fiber is configured to irradiated onto a treatment target in a state in which the injection needle is inserted into skin, the distal end of the optical fiber is positioned on an inner side of the opening of the injection needle, and the protector is positioned further towards the opening side of the injection needle than the distal end of the optical fiber.

DETAILED DESCRIPTION OF EMBODIMENTS

An optical treatment device 1 according to a first embodiment of some embodiments will be described hereinafter with reference to the drawings.

Figure 1:
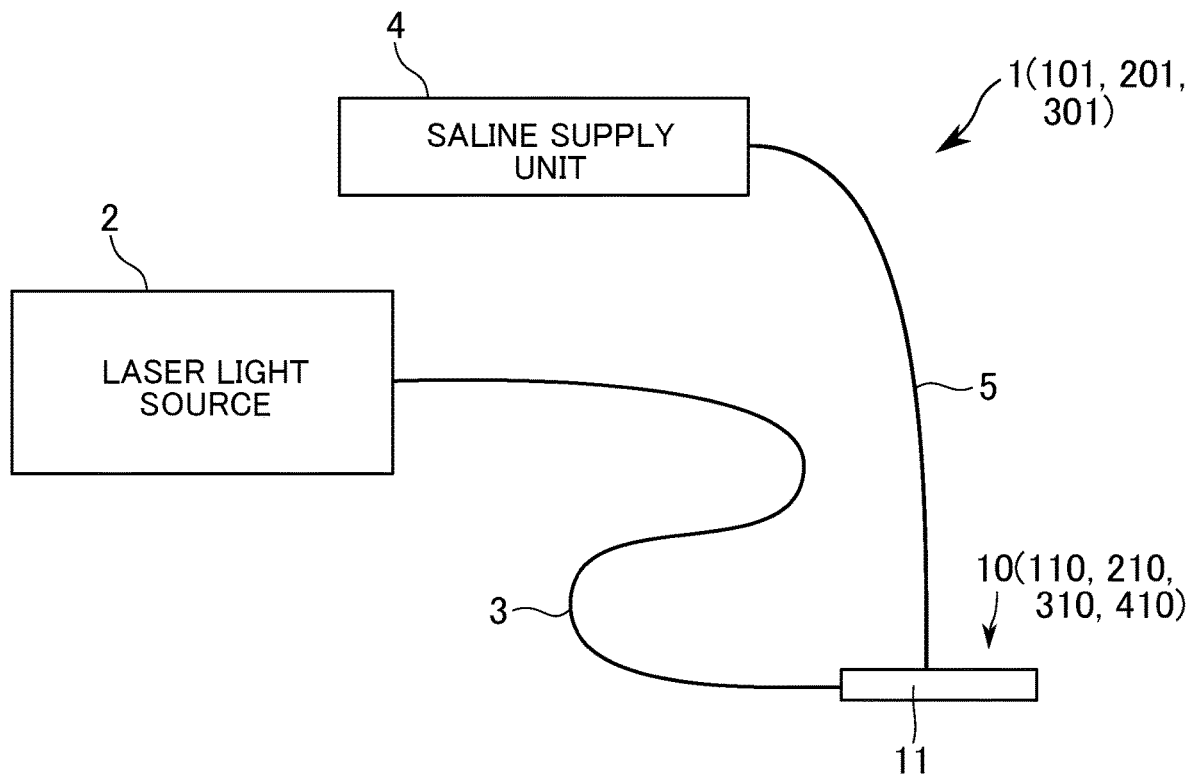
FIG. 1 is an overall configuration diagram of an optical treatment device according to some embodiments.
Figure 2:
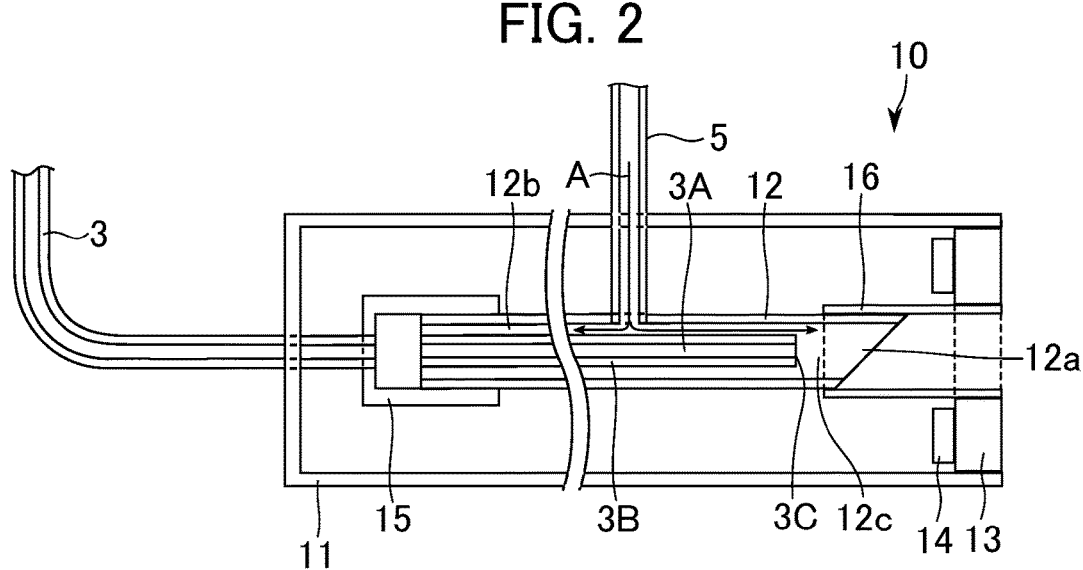
FIG. 2 is a configuration diagram of an injection needle unit according to a first embodiment.

FIG. 1 is an overall configuration diagram of an optical treatment device 1 according to the first embodiment. FIG. 2 is a configuration diagram of an injection needle unit according to the first embodiment.

The optical treatment device 1 includes a laser light source 2, an optical fiber 3, a saline supply unit 4, a tube 5, and an injection needle unit 10.

The laser light source 2 emits laser light having a wavelength in the range of 315 to 1100 nm. The laser light source 2 is constituted by, for example, a diode-pumped solid-state laser, each having a wavelength of 532 nm. It is preferable for the pulse width of the laser light to be 0.1 to 50 msec, and the energy density of laser irradiation to be 0.1 to 20 J/cm². Further, the light source is not limited to a laser light source, that is, any light source may be used as long as light emitted thereby is within the wavelength range described above, and incoherent light of 1 W or more may also be used.

A proximal end of the optical fiber 3 is connected to the laser light source 2 and, as shown in FIG. 2, the optical fiber 3 includes a core 3A through which laser light from the laser light source 2 propagates and a clad 3B which covers the core 3A.

The saline supply unit 4 includes, for example, a syringe pump. The saline supply unit 4 is configured to supply saline, which is a protector and serves as a liquid that can be injected into a living body, via a tube 5 to the injection needle unit 10 at a desired speed.

The injection needle unit 10 includes a case 11, an injection needle 12, a stopper 13, a Peltier element 14, a motorized stage 15, and an injection needle guide 16.

The case 11 has, for example, a cylindrical shape which is open at one end and closed at the other end. The optical fiber 3 and the tube 5 pass through the case 11.

The injection needle 12 is disposed in the case 11. The tube 5 is connected to the injection needle 12. The injection needle 12 is made of, for example, stainless steel, has a size of 25 gauge or less and, as shown in FIG. 2, has an opening 12a at a distal end thereof. The optical fiber 3 is inserted into a hole 12c of the injection needle 12, and a distal end 3C thereof is positioned on an inner side of the opening 12a of the injection needle 12. A gap 12b is formed between the inner peripheral surface of the injection needle 12 and the outer peripheral surface of the optical fiber 3. As a result, saline solution A supplied from the saline supply unit 4 flows into the gap 12b via the tube 5 and is discharged to the outside from the opening 12a.

The stopper 13 has, for example, an annular shape, and is inserted in the opening of the case 11. During treatment, the distal end of the injection needle 12 protrudes from the stopper 13 at a desired length (for example, 0.2 to 3 mm) so as to reach a layer of the skin below the epidermis. The stopper 13 restricts the injection needle 12 from entering the skin by a desired length or longer. As the injection needle 12 is to be inserted into different areas of the skin, the stopper 13 may have a structure that allows a position thereof with respect to the case 11 to be changed in accordance with the thickness of the epidermis or dermis in different areas. The stopper 13 may be made of, for example, resin, glass, metal, or the like, and a Peltier element or the like may be attached to the stopper 13 to enable cooling of the skin surface. The stopper 13 itself may be a Peltier element or the like.

The Peltier element 14 is attached to the stopper 13 in the case 11 and cools the skin surface via the stopper 13.

The motorized stage 15 causes the injection needle 12 to reciprocate along its own axis, causing a part of the injection needle 12 to protrude from the case 11, or returning the protruded injection needle 12 into the case 11. Due to the motorized stage 15, the injection needle 12 moves by a predetermined distance only, so that the distal end of the injection needle 12 protrudes from the stopper 13 by a desired length.

The injection needle guide 16 has a cylindrical shape, is attached to the inner periphery of the stopper 13 and guides the reciprocal motion of the injection needle 12 by the motorized stage 15. The injection needle guide 16 constitutes a part of the stopper 13.

Next, a method of using the optical treatment device 1 according to the first embodiment will be described with reference to FIG. 3.

Figure 3:
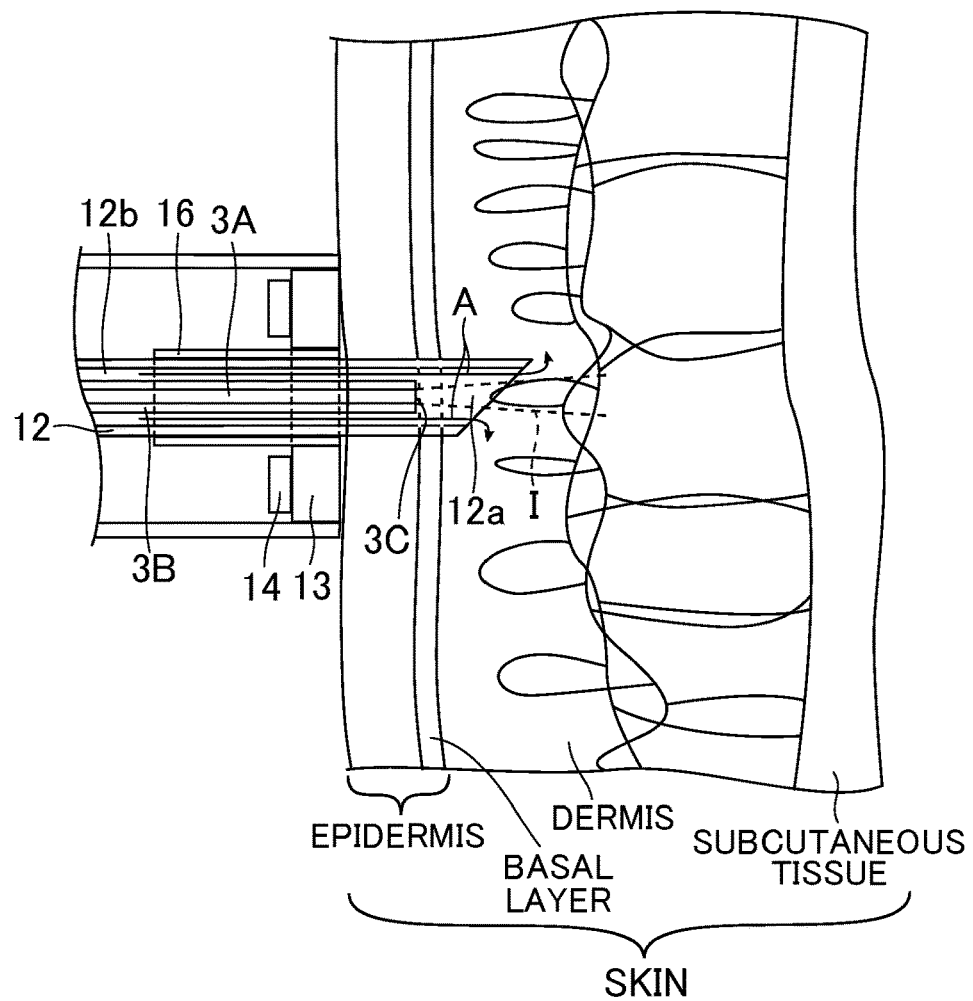
FIG. 3 is a diagram showing a usage state of the optical treatment device according to the first embodiment.

FIG. 3 is a diagram showing a usage state of optical treatment device 1 according to first embodiment.

With the stopper 13 in contact with the skin surface, the injection needle 12 is propelled forward by the motorized stage 15, causing the injection needle 12 to enter the skin of a treatment target area. Due to the stopper 13 being in contact with the skin surface, the injection needle 12 enters the skin by a desired length only from the stopper 13. As a result, the distal end of the injection needle 12 reaches the dermis, which is beyond the melanosomes present in the epidermis. In addition, saline is supplied from the saline supply unit 4 so as to pass through the gap 12b as indicated by arrow A, and the saline is injected into the living body from the opening 12a. For this reason, living tissue does not come into contact with the distal end 3C of the optical fiber 3.

In this state, laser light I is emitted from the distal end 3C of the optical fiber 3 due to output of a laser having a predetermined pulse width from the laser light source 2, and the laser is irradiated onto a vessel in the treatment target area. As a result, the laser light I, which is output in the predetermined wavelength region, is more strongly absorbed by hemoglobin than by other tissue, whereby the temperature of the vessel is raised, causing damage to the vessel.

With the optical treatment device 1 according to the first embodiment, the laser light I is irradiated onto the treatment target from the optical fiber 3 in a state in which the injection needle 12 is inserted into skin, the distal end 3C of the optical fiber 3 is positioned on an inner side of the opening 12a of the injection needle 12, and the saline is positioned further towards the opening 12a side of the injection needle 12 than the distal end 3C of the optical fiber 3.

With this configuration, the laser light I is not absorbed by melanosomes present in the epidermis, hence the laser light I can be radiated onto a vessel, that is, the treatment target, without being substantially dissipated. Accordingly, the laser light I can be reliably and efficiently irradiated onto the vessel, that is, the treatment target, and reoccurrence of a vascular lesions can be suppressed.

Further, living tissue can be prevented from adhering to the distal end 3C of the optical fiber 3 due to saline being interposed between the distal end 3C of the optical fiber 3 and the opening 12a of the injection needle 12. Accordingly, it is possible to prevent the living tissue from being burned onto the distal end 3C of the optical fiber 3, enabling treatment to be performed continuously. Further, as saline is injected into the living body from the injection needle 12, heat damage to surrounding tissue can be suppressed.

Further, the stopper 13 is positioned around the outer side of the injection needle 12 and restricts the injection needle 12 from entering the skin by a desired length or longer. That is, the distal end of the injection needle 12 protrudes from the stopper 13 by a predetermined length, and the stopper 13 comes into contact with the surface of the skin, whereby the injection needle 12 is restricted from entering the skin by a desired length or longer. Accordingly, the injection needle 12 can always be inserted to a desired position. Note that it is preferable for the length at which the injection needle 12 is inserted into the skin to be the range of 0.2 to 3 mm.

Further, as the stopper 13 is cooled by the Peltier element 14 and, in turn, the skin is cooled by the stopper 13, heat damage to surrounding tissue can be suppressed. Moreover, this cooling effect also has the effect of alleviating pain on the basis of Gate Control Theory.

The optical treatment device 101 according to a second embodiment of some embodiments will be described hereinafter with reference to FIG. 4. Note that members which are identical to those of the optical treatment device 1 according to the first embodiment will be denoted by the same reference numerals and description thereof omitted, and only parts which differ will be described.

Figure 4:
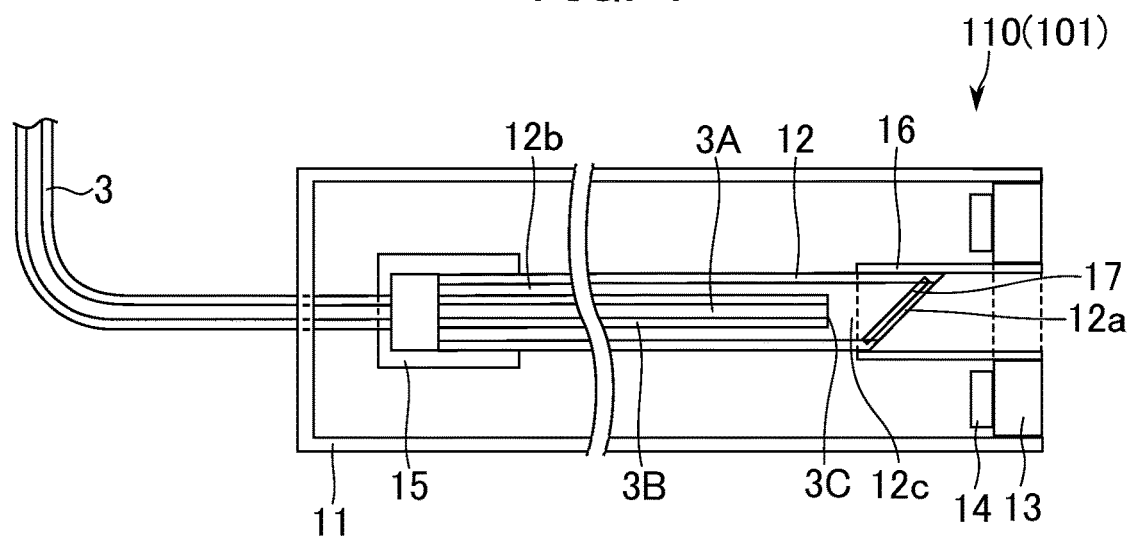
FIG. 4 is a configuration diagram of an injection needle unit according to a second embodiment.

FIG. 4 is a configuration diagram of the injection needle unit 110 according to the second embodiment.

In the second embodiment, a glass 17 which is capable of transmitting a laser is provided so as to plug the hole 12c of the injection needle 12. Since the glass 17 is capable of preventing living tissue from adhering to the distal end 3C of the optical fiber 3, it is possible to prevent the living tissue from being burned onto the distal end 3C of the optical fiber 3.

Further, in the optical treatment device 101 according to the second embodiment, the laser light is irradiated onto the treatment target from the optical fiber 3 in a state in which the injection needle 12 is inserted into the skin, the distal end 3C of the optical fiber 3 is positioned on an inner side of the opening 12a of the injection needle 12, and the glass 17 is positioned further towards the opening 12a side of the injection needle 12 than the distal end 3C of the optical fiber 3.

With this configuration also, the laser light is not absorbed by melanosomes present in the epidermis, hence the laser light can be radiated onto a vessel, that is, the treatment target, without being substantially dissipated. Accordingly, the laser light can be reliably and efficiently radiated onto the vessel, that is, the treatment target, and the reoccurrence of vascular lesions can be suppressed. Note that, with the configuration according to this embodiment, saline cannot be injected into the living body via the injection needle 12, hence it is not necessary to provide the saline supply unit 4.

The optical treatment device 201 according to a third embodiment of some embodiments will be described hereinafter with reference to FIG. 5. Note that members which are identical to those of the optical treatment device 1 according to the first embodiment will be denoted by the same reference numerals and description thereof omitted, and only parts which differ will be described.

Figure 5:
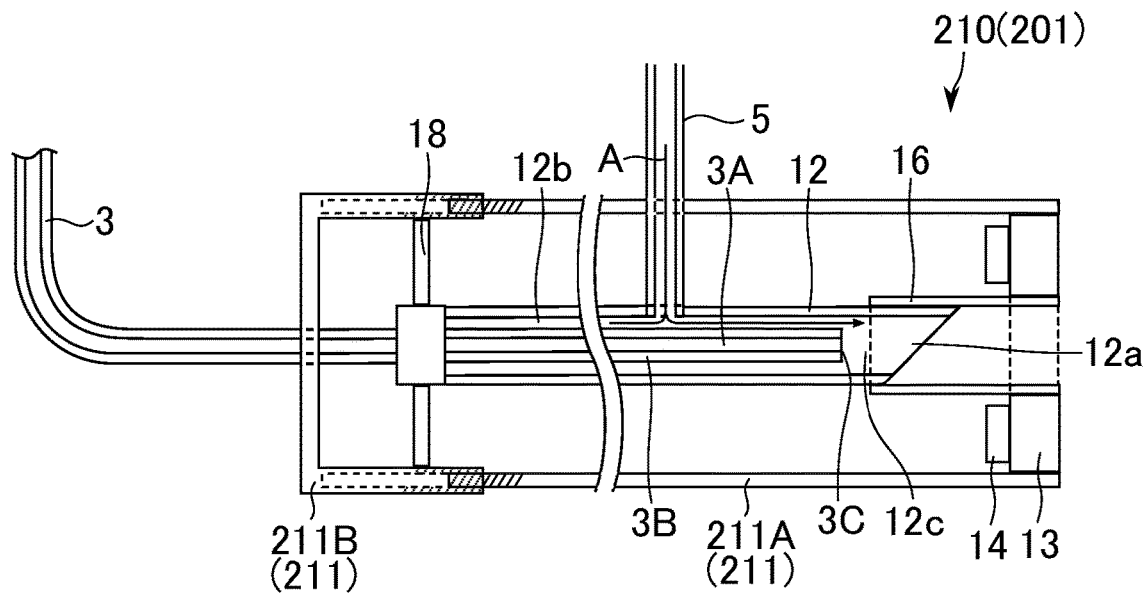
FIG. 5 is a configuration diagram of an injection needle unit according to a third embodiment.

FIG. 5 is a configuration diagram of the injection needle unit 210 according to the third embodiment.

In the third embodiment, the case 211 includes a first case 211A and a second case 211B. The first case 211A has, for example, a cylindrical shape, and a threaded portion is formed at an end thereof on a side opposite to the side at which the stopper 13 is provided. The second case 211B has a cylindrical shape which is open at one end and closed at the other end, and a threaded portion is formed therein. The threaded portion of the first case 211A and the threaded portion of the second case 211B engage with each other, and a configuration thereof is such that, by automatically or manually rotating the second case 211B, the second case 211B is reciprocated relative to the first case 211A.

The injection needle 12 is fixed to the second case 211B by a fixture 18. The injection needle 12 is configured so as not to rotate even if the second case 211B rotates. By automatically or manually rotating the second case 211B, a part of the injection needle 12 is caused to protrude from the case 211, or the protruding injection needle 12 is returned into the case 211.

This configuration and, in turn, the optical treatment device 201 according to this embodiment, also achieves the same effect as the optical treatment device 201 according to the first embodiment. Note that this embodiment may also be configured so that injection needle 12 also rotates when the second case 211B rotates. Moreover, a configuration may be adopted in which the injection needle 12 is moved by pushing down on the second case 211B.

An optical treatment device 301 according to a fourth embodiment of some embodiments will be described hereinafter with reference to FIG. 6. Note that members which are identical to those of the optical treatment device 1 according to the first embodiment will be denoted by the same reference numerals and description thereof omitted, and only parts which differ will be described.

Figure 6:
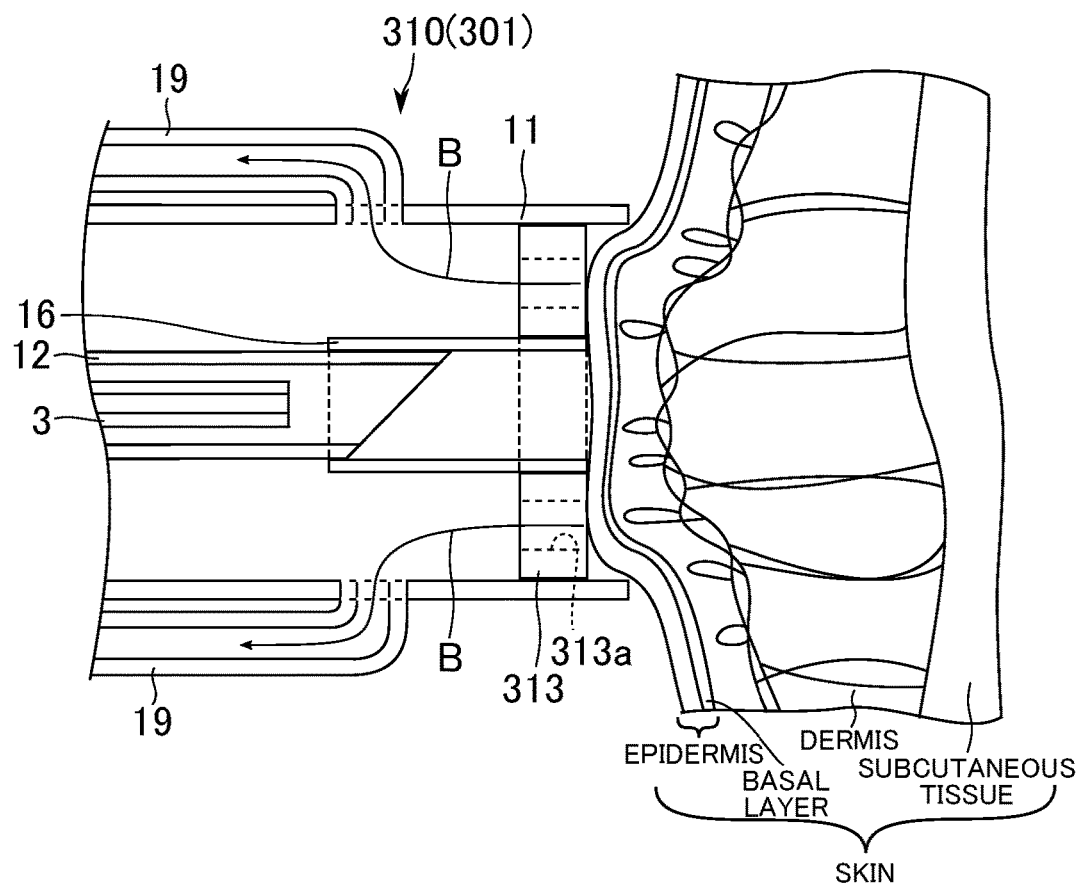
FIG. 6 is an enlarged view of a vicinity of a distal end of an injection needle unit according to a fourth embodiment and a usage state thereof.

FIG. 6 is an enlarged view of the vicinity of the distal end of the injection needle unit 310 according to the fourth embodiment and a usage state thereof.

A suction tube 19 is connected to the case 11, and a suction pump (not shown) is connected to the suction tube 19. A through hole 313a, which communicates between the inside and the outside of case 11, is formed in the stopper 313, and allows air outside the case 11 to be sucked into the suction tube 19 via the through hole 313a, as indicated by arrow B, by driving the suction pump (not shown).

When the optical treatment device 301 is in use, the skin is aspirated and brought into contact with the stopper 313 as shown in FIG. 6. In this state, the injection needle 12 is inserted into the skin, and laser light is irradiated from the distal end 3C of the optical fiber 3.

The optical treatment device 301 according to this embodiment also achieves the same effect as the optical treatment device 1 according to the first embodiment. Further, due to the suction means (the suction pump (not shown) and the suction tube 19), the injection needle 12 can be inserted into the skin in a state in which the skin is aspirated and brought into contact with the stopper 313, whereby variations in the length at which the injection needle is inserted into the skin can be further suppressed.

Further, by forming the stopper 313 formed with the through hole 313a from a Peltier element, pain can be relieved on the basis of Gate Control Theory using suction and cooling.

Note that the present disclosure is not limited to some embodiments described above. Those skilled in the art would be capable of making various additions and/or modifications within the scope of the present disclosure.

In the embodiments described above, the optical treatment device 1, 101, 201 and 301 is applied as a device for treating vascular lesions, but may also be applied as a device for, to give examples, skin rejuvenation, slimming, or tattoo removal. Skin rejuvenation leads to improvement of fine lines and improvement of skin quality by promoting contraction and generation of collagen in the dermis. Slimming is, in this context, laser irradiation that targets fat, and leads to localized improvements in appearance by melting fat. Further, concerning tattoo removal, the optical treatment device 1, 101, 201 and 301 is effective for removing pigments located deeper in the skin, and is effective at depths at which laser irradiation from the epidermis is ineffective.

In some embodiments described above, a diode-pumped solid-state laser is used as the light source, but another laser light source, such as a solid-state laser, a liquid laser such as a dye laser, or a gas laser may also be used as long as the laser thereof is capable of being output at a predetermined wavelength.

In the first embodiment, saline is used as the protector, but water, a photosensitizer, or a fluorescent dye may also be used. In the second embodiment, glass is used as the protector, but quartz or a resin capable of transmitting light may also be used. Moreover, although the stopper 13 is cooled by the Peltier element 14, it is also possible to employ a system in which water or the like is circulated through the interior of the stopper 13.

Further, in the embodiments described above, the wavelength is set as 315 to 1100 nm, but when targeting skin rejuvenation or fat, an infrared wavelength may be selected. When targeting fat or tattoos, the length at which the injection needle 12 is inserted into the skin may be 3 mm or longer.

Figure 7:
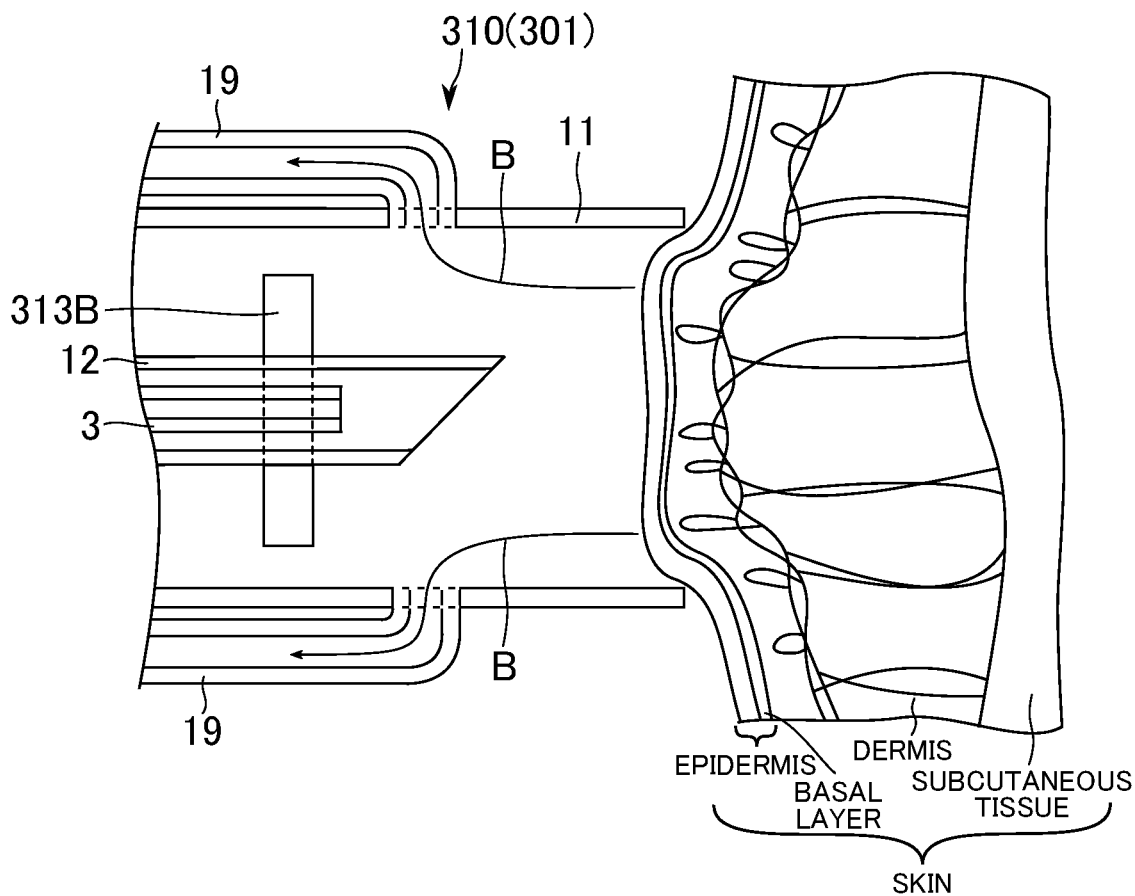
FIG. 7 is an enlarged view of a vicinity of a distal end of an injection needle unit according to a modification to some embodiments and a usage state thereof.

Further, as a modified example of the optical treatment device 301 according to the fourth embodiment, the injection needle unit 310 may be configured so that, as shown in FIG. 7, the stopper 313B is provided around the outer periphery of the injection needle 12 and is attached thereto at a position which is a desired distance from the distal end of the injection needle 12. This configuration also enables the injection needle 12 to be restricted from entering the skin by a desired length or longer.

Figure 8:
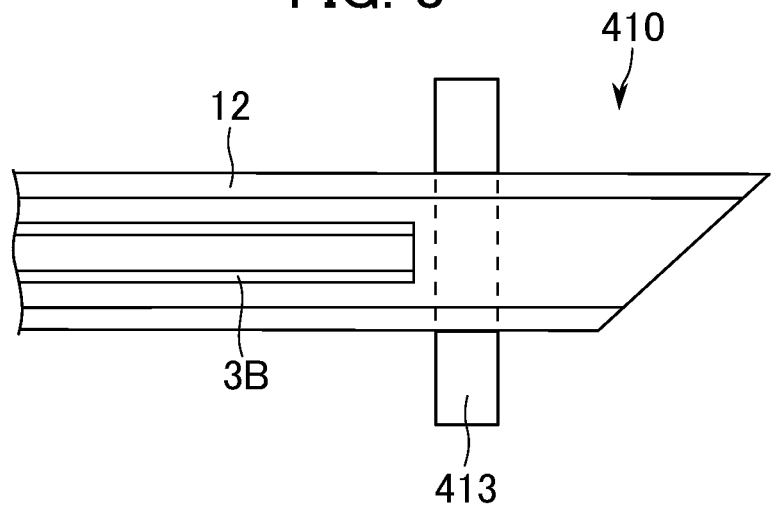
FIG. 8 is an enlarged view of a vicinity of a distal end of an injection needle unit according to a modification to some embodiments.

As another modified example of the optical treatment device, the injection needle unit 410 may be, as shown in FIG. 8, constituted by the injection needle 12, the stopper 413 wrapped around the periphery of the injection needle 12, and a needle reciprocating mechanism (not shown), without providing the case 11.

Concerning electrical driving of the motorized stage 15 and the like, an element that is capable of converting an electric signal into a mechanical operation, such as a solenoid, a motor, a piezoelectric element, may be used. Moreover, irradiation of the laser light from the optical fiber 3 may be started immediately after the injection needle has been inserted in the skin, or before the injection needle 12 has been inserted in the skin. Further, a distance sensor, a pressure sensor, a temperature sensor, or the like may be used to determine whether or not the stopper 13 is contact with the skin.

What is claimed is:

1. An optical treatment device comprising:
a light source configured to output light;
an injection needle having an opening at a distal end thereof and defining a hole therein;
an optical fiber configured to output the light from the light source and inserted in the hole in the injection needle, the optical fiber having a distal end positioned on an inner side of the opening of the injection needle;
a stopper that is separate from the injection needle, is positioned around an outer side of the injection needle, and restricts the injection needle from entering the skin by a desired length or longer; and
a protector configured to transmit the light emitted from the optical fiber, positioned further towards an opening side of the injection needle than the distal end of the optical fiber, and configured to prevent adherence of tissue to the optical fiber, wherein:
the distal end of the injection needle is sharp, and
the light emitted from the optical fiber is configured to be irradiated onto a treatment target in a state in which the injection needle is inserted into skin, the distal end of the optical fiber is positioned on an inner side of the opening of the injection needle, and the protector is positioned further towards the opening side of the injection needle than the distal end of the optical fiber.

2. The optical treatment device according to claim 1, wherein
the protector is a liquid that is capable of being injected into a living body by passing through a gap between an inner surface of the injection needle and an outer surface of the optical fiber, and is supplied further towards the opening side of the injection needle than the distal end of the optical fiber.

3. The optical treatment device according to claim 1, wherein
the protector is provided at a position further towards the opening side of the injection needle than the distal end of the optical fiber and plugs the hole of the injection needle, and
the protector is made of glass, quartz, or resin capable of transmitting light.

4. The optical treatment device according to claim 1, wherein the stopper has a cooling function.

5. The optical treatment device according to claim 1, comprising:
a suction unit attachment configured to aspirate the skin to bring the skin into contact with the stopper.

6. The optical treatment device according to claim 1, wherein
the stopper includes a guide portion that is provided along an inner periphery of the stopper to guide movement of the injection needle.

* * * * *